United States Patent [19]

Skinner et al.

[11] Patent Number: 5,066,492

[45] Date of Patent: Nov. 19, 1991

[54] METHOD OF TREATING HERPES SIMPLEX VIRUS

[75] Inventors: Gordon R. B. Skinner, Solihull; Alexander Buchan, Birmingham, both of England

[73] Assignee: University of Birmingham, England

[21] Appl. No.: 528,344

[22] Filed: May 25, 1990

Related U.S. Application Data

[63] Continuation of Ser. No. 21,491, Mar. 4, 1987, abandoned.

[30] Foreign Application Priority Data

Mar. 5, 1986 [GB] United Kingdom ............... 8605390

[51] Int. Cl.$^5$ ..................... A61K 39/12; C12N 7/00
[52] U.S. Cl. ................................ 424/89; 424/85.8; 424/86; 435/235.1; 435/236; 435/237
[58] Field of Search ............... 424/89, 85.8, 86; 435/235, 236, 237

[56] References Cited

U.S. PATENT DOCUMENTS

| | | | |
|---|---|---|---|
| 3,660,234 | 5/1972 | Gray | 424/89 |
| 4,039,656 | 8/1977 | Straub | 424/85 |
| 4,374,127 | 2/1983 | Larson et al. | 424/89 |

FOREIGN PATENT DOCUMENTS 1183083  2/1985  Canada .................. 424/89

OTHER PUBLICATIONS

Sterz et al., *Intervirology*, vol. 2, pp. 1–13, 1973/74.
Sterz et al., "Immunologic and Genetic Relationship Between Herpes Simplex Virus and Bovine Herpes Mammillitis Virus", Intervirology, vol. 2, pp. 1–13, 1973/74.
Poli et al., "Serological Comparison of Bovid Herpesvirus and Herpes Simplex Virus by Reciprocal Neutralization Kinetic Studies", Comp. Immun. Microbiol. Infect. Dis.–vol. 3, pp. 509–515 (1980).
Castrucci et al., "A Study in Calves of an Immunologic Relationship Between Herpes Simplex Virus and Bovid Herpesvirus", Comp. Immun. Microbiol. Infect. Dis. vol. 4, pp. 1–7 (1981).
Birch et al., "Replication of Type 2 Herpes Simplex Virus in Human Endocervical Tissue in Organ Culture", Br. J. Exp. Path. vol. 57, p. 460 (1976).
Skinner et al., "Role of Bovine Mammallitis Virus Towards Preparation of an Alternative Vaccine Against Herpes Simplex Virus Infections of Human Subjects", Biol. Abstr. 83(11), AB-867, Ref. #111174, 1987.
Schneweis et al., "The Influence of Different Modes of Immunization on the Experimental Genital Herpes Simplex Virus Infection of Mice", Biol. Abstr. 73(6): 4037, Ref. #39148, 1981.

*Primary Examiner*—Margaret Moskowitz
*Assistant Examiner*—Abdel A. Mohamed
*Attorney, Agent, or Firm*—Leydig Voit & Mayer

[57] ABSTRACT

A method of treating or preventing infection of a human subject is provided which includes inoculation of the subject with bovine mammilitis virus.

3 Claims, No Drawings

METHOD OF TREATING HERPES SIMPLEX VIRUS

This application is a continuation of application Ser. No. 07/021,491 filed Mar. 4, 1987 and now abandoned.

This invention relates to a vaccine against human herpes simplex and to a method of its production. The invention resides principally in the use of bovine mammillitis virus for manufacture of a vaccine against herpes simplex virus (HSV).

Both human herpes simplex virus Type 1 (HSV1) and Type 2 (HSV2) have been shown to be capable of causing neonatal infections and there is an association between HSV2 infections of the human cervix and cancer of that organ. There is thus a need for a vaccination programme towards prevention of HSV infection in human subjects, and a number of research projects are currently directed towards developing inactivated vaccines against HSV. The preparation of such inactivated vaccines involves considerable time and expenditure, particularly with respect to removal of virus particles and intraparticulate virus DNA which may have infectious or oncogenic complications in a human subject.

It has been shown by Sterz et al, Intervirology 1973-74, 2, 1-13, Poli et al, Comp. Immunol. Microbiol. Infect. Dis. 1980, 3, 509-515 and Castrucci et al, Comp. Immunol. Microbiol. Infect. Dis. 1981, 4, 1-7 that bovine mammillitis virus (BMV) shares cross-reacting antigens with a number of herpes viruses, particularly HSV1 and HSV2. These cross-reacting antigens have been identified by neutralisation tests, solid phase radioimmune assays and by Western blotting techniques where the polypeptides of the virus are immobilised on gels or are transferred to nitro-cellulose prior to immunological identification. More especially, there is evidence that vaccination of animal species with BMV will protect against subsequent challenge with HSV and that live virus appears to provide a greater level of protection than virus which has been inactivated in some way. Tests of BMV replication in human tissue were carried out following the procedure of Birch et al, Br. J. Exp. Pathol. 1976, 57, 460-671. Explants of human tissue were placed in a virus suspension containing approximately $10^7$ plaque forming units and agitated at 37° C. for 2 hours. Explants were removed from the virus suspension, washed thoroughly in medium and placed in hyperimmune antiserum at a 1 in 10 dilution for a further hour at 37° C. to remove input virus; a sample of organ culture was then rewashed and resuspended in 1 ml of sterile $H_2O$ and stored at $-70°$ C. for future titration, thereby providing an index of input virus. The explants were cultured at 37° C. and explants removed and placed into 1 ml aliquot of sterile water at various time intervals thereafter. Under these conditions herpes simplex virus will replicate in tissue explants with an increase of over 1000 fold in virus titre.

Neither virus replication nor virus cytopathic effect was detectable in He La, He P or He L (MRCA) cell lines, or in a human explant culture. As positive controls in these experiments it was required that under the same conditions HSV would replicate to usual titres in human explants and that BMV would replicate to usual titres- .in hamster kidney cells.

Serological evidence was sought of prior infection of human subjects with BMV, these subjects being drawn from the general population and from long-term workers with BMV. Augmented neutralising tests following the procedure of Holmes et al, Med. Microbiol. Immunol. 1985, 174, 167-175 were carried out using BMV antigens and did not reveal BMV specific antibody in any case.

Additionally two laboratory mishaps have been observed which resulted in accidental inoculation of BMV. In one case a thumb was pricked with BMV infected cell extract (Allerton strain at $3 \times 10^8$ plaque forming units/ml) and in the other a BMV virus suspension (Allerton strain at $2 \times 10^7$ plaque forming units/ml) was sprayed into an eye. There was no local or general evidence of virus infection in either case.

There is therefore no evidence that human subjects have been naturally infected by BMV or that this virus is capable of infecting human cells or human organ cultures under laboratory conditions. Though therefore at this stage it is not possible to completely rule out the possibility of infection of human subjects by BMV, there appears a high probability that BMV will merely serve as an unadulterated source of virus antigen which is more efficient than the inactivated vaccines presently proposed.

According to the invention bovine mammillitis virus is used to prepare a vaccine against herpes simplex virus infection in human subjects.

According to a further aspect of the invention a method of preparing a vaccine against herpes simplex virus infection in human subjects comprises infecting host cells with bovine mammillitis virus and separating the infected cells to provide a supernatant which is substantially free of serum and of the host cells, said supernatant providing the active constituent of the vaccine. The term virus particle used herein is to be understood as relating to the entire virus structure, comprising nucleic acid (in the case of bovine mammillitis virus DNA) surrounded by a protein shell or capsid. Some particles of bovine mammillitis virus also include a glycoprotein envelope surrounding the protein shell, in which case the term virus particle also includes the virus envelope.

In an example of the invention, described by way of example only, monolayer cultures of a suitable cell line are serum-starved for 24 hours and then thoroughly washed. A strain ("Allerton" strain) of bovine mammillitis virus (BMV) is stored in a serum-free medium and used to infect the serum-starved cell cultures at a multiplicity of one plaque-forming unit per cell. After infection the cell cultures are incubated for 24 hours at 37° C. in a carbon dioxide enhanced environment and in a medium which does not contain serum or tryptose phosphate broth. At the end of the 24 hours incubation period the medium containing virus particles is separated by centrifugation and collected. A sample of the incubation medium which is free of both host cells and serum is plaque titrated in a suspension of baby hamster kidney (BHK21) cells, by the method of Russell et al, Nature 1962, 195, 1208, to quantify the amount of virus present.

A supernatant of the aforesaid incubation medium constitutes a live virus inoculum which is further titrated and adjusted to a concentration of $10^6$ infectious virus units per milliliter this concentration being suitable for inoculation into human subjects.

Alternatively the virus particles in the incubation medium are further purified by centrifuging in a sucrose gradient and collection of a required band from the gradient, following which the virus particles are resuspended in phosphate buffer saline and re-titrated.

In a further alternative the separated virus particles are inactivated, for example by treatment with formalin or exposure to ultra violet light, these inactivated particles forming the effective constituent of a vaccine.

It is envisaged that the resulting inoculant would be administered to subjects who may be at risk of herpes infection, to prevent their contracting this infection, and for subjects who have already contracted the infection in order to modify the future pattern and outcome of their infection. The vaccine may be administered either by subcutaneous inoculation of the upper arm or by intracutaneous inoculation at the same site. It is envisaged that 6 vaccinations will be administered at weekly intervals.

We claim:

1. A method of preventing or treating herpes simplex infection of a human subject comprising inoculation of said subject with bovine mammillitis virus.

2. A method as claimed in claim 1 wherein said bovine mammillitis virus is the Allerton strain.

3. A method of preventing or treating herpes simplex infection of a human subject, comprising inoculation of said subject with bovine mammillitis virus particles in a medium which is substantially free of cellular material and DNA from host cells used for incubation of the virus.

* * * * *

UNITED STATES PATENT AND TRADEMARK OFFICE
CERTIFICATE OF CORRECTION

PATENT NO. : 5,066,492

DATED : November 19, 1991

INVENTOR(S) : Skinner et al

It is certified that error appears in the above-identified patent and that said Letters Patent is hereby corrected as shown below:

On the title page:

In item no. [54], Title, change "Method Of Treating Herpes Simplex Virus" to --Method Of Treating Herpes Simplex Virus Infection--.

Signed and Sealed this

Nineteenth Day of October, 1993

*Attest:*

BRUCE LEHMAN

*Attesting Officer*   *Commissioner of Patents and Trademarks*